United States Patent [19]

Merrifield et al.

[11] Patent Number: 5,665,705
[45] Date of Patent: *Sep. 9, 1997

[54] GLUCAGON ANALOGS WITH SERINE REPLACEMENTS

[75] Inventors: Robert B. Merrifield, Cresskill, N.J.; Cecilia G. Unson, New York, N.Y.

[73] Assignee: The Rockefeller University, New York, N.Y.

[*] Notice: The term of this patent shall not extend beyond the expiration date of Pat. No. 5,480,867.

[21] Appl. No.: 473,334

[22] Filed: Jun. 7, 1995

Related U.S. Application Data

[63] Continuation-in-part of Ser. No. 255,558, Jun. 8, 1994, Pat. No. 5,480,867, which is a continuation of Ser. No. 175,137, Dec. 29, 1993, abandoned.

[51] Int. Cl.[6] .................... A61K 38/26; C07K 14/00; C07K 14/605
[52] U.S. Cl. .................................. 514/12; 530/308
[58] Field of Search ........................... 514/12; 530/308

[56] References Cited

U.S. PATENT DOCUMENTS 4,879,273 11/1989 Merrifield et al. .
5,143,902 9/1992 Merrifield et al. .

FOREIGN PATENT DOCUMENTS

WO92/04042 3/1992 WIPO .
WO92/12998 8/1992 WIPO .

OTHER PUBLICATIONS

Flanders et al. (1984) J. Biol. Chem. 259:7031–7.
Unson et al., (1994) J. Biol. Chem 269:12548–51.
Unson et al. (1994) Proc. Natl. Acad. Sci. USA 91:454–58.
Unson et al. (1993) Arch. Biochem. Biophys. 300:747–50.
Unson et al. (1991) J. Biol. Chem. 266:2763–66.
Unson et al. (1989) J. Biol. Chem. 264:789–94.
Breddam et al. (1987) Carlsberg Res. Commun. 55–63.
Unson et al. (1987) Biochemistry 84:4083–7.

*Primary Examiner*—Paula K. Hutzell
*Assistant Examiner*—Benet Prickril
*Attorney, Agent, or Firm*—Klauber & Jackson

[57] ABSTRACT

Glucagon analogs characterized principally by substitution of amino acid residues at positions 9, 11, 16, and 21 with or without a histidine residue at the amino terminus are useful adjuncts to insulin therapy.

30 Claims, No Drawings

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide
        ( A ) DESCRIPTION: glucagon ( i i i ) HYPOTHETICAL: No ( i v ) ANTI-SENSE: NO ( x i ) SEQUENCE DESCRIPTION: SEQ ID NO:1:

```
His Ser Gln Gly Thr Phe Thr Ser Asp Tyr Ser Lys Tyr Leu Asp Ser
 1               5                  10                  15
Arg Arg Ala Gln Asp Phe Val Gln Trp Leu Met Asn Thr
            20                  25
```

( 2 ) INFORMATION FOR SEQ ID NO:2:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide
        ( A ) DESCRIPTION: glucagon analog ( i i i ) HYPOTHETICAL: No ( i v ) ANTI-SENSE: NO ( x i ) SEQUENCE DESCRIPTION: SEQ ID NO:2:

```
Ser Gln Gly Thr Phe Thr Ser Gly Tyr Ser Lys Tyr Leu Asp Ser
 1               5                  10                  15
Arg Arg Ala Gln Asp Phe Val Gln Trp Leu Met Asn Thr
            20                  25
```

( 2 ) INFORMATION FOR SEQ ID NO:3:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide
        ( A ) DESCRIPTION: glucagon analog ( i i i ) HYPOTHETICAL: No ( i v ) ANTI-SENSE: NO (ix) FEATURE:
    (D) OTHER INFORMATION: Xaa represents Nle (xi) SEQUENCE DESCRIPTION: SEQ ID NO:3:

Ser Gln Gly Thr Phe Thr Ser Xaa Tyr Ser Lys Tyr Leu Asp Ser
1               5                   10                  15

Arg Arg Ala Gln Asp Phe Val Gln Trp Leu Met Asn Thr
                20                  25

(2) INFORMATION FOR SEQ ID NO:4:

(i) SEQUENCE CHARACTERISTICS:
      (A) LENGTH: 28 amino acids
      (B) TYPE: amino acid
      (C) STRANDEDNESS: single
      (D) TOPOLOGY: linear (ii) MOLECULE TYPE: peptide
      (A) DESCRIPTION: glucagon analog (iii) HYPOTHETICAL: No (iv) ANTI-SENSE: NO (xi) SEQUENCE DESCRIPTION: SEQ ID NO:4:

Ser Gln Gly Thr Phe Thr Ser Lys Tyr Ser Lys Tyr Leu Asp Ser
1               5                   10                  15

Arg Arg Ala Gln Asp Phe Val Gln Trp Leu Met Asn Thr
                20                  25

(2) INFORMATION FOR SEQ ID NO:5:

(i) SEQUENCE CHARACTERISTICS:
      (A) LENGTH: 28 amino acids
      (B) TYPE: amino acid
      (C) STRANDEDNESS: single
      (D) TOPOLOGY: linear (ii) MOLECULE TYPE: peptide
      (A) DESCRIPTION: glucagon analog (iii) HYPOTHETICAL: No (iv) ANTI-SENSE: NO (xi) SEQUENCE DESCRIPTION: SEQ ID NO:5:

Ser Gln Gly Thr Phe Thr Ser Glu Tyr Ser Lys Tyr Leu Asp Ser
1               5                   10                  15

Arg Arg Ala Gln Asp Phe Val Gln Trp Leu Met Asn Thr
                20                  25

(2) INFORMATION FOR SEQ ID NO:6:

(i) SEQUENCE CHARACTERISTICS:
      (A) LENGTH: 28 amino acids
      (B) TYPE: amino acid
      (C) STRANDEDNESS: single
      (D) TOPOLOGY: linear (ii) MOLECULE TYPE: peptide
      (A) DESCRIPTION: glucagon analog (iii) HYPOTHETICAL: No (iv) ANTI-SENSE: NO (xi) SEQUENCE DESCRIPTION: SEQ ID NO:6:

Ser Gln Gly Thr Phe Thr Ser Glu Tyr Ser Lys Tyr Leu Asp Ser
1               5                   10                  15

```
        Lys  Lys  Ala  Gln  Glu  Phe  Val  Gln  Trp  Leu  Met  Asn  Thr
                       20                       25
```

(2) INFORMATION FOR SEQ ID NO:7:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: peptide
        (A) DESCRIPTION: glucagon amide (iii) HYPOTHETICAL: No (iv) ANTI-SENSE: NO (ix) FEATURE:
        (A) NAME/KEY: amide group substitution for carboxyl group
        (D) OTHER INFORMATION: Xaa represents Nle (xi) SEQUENCE DESCRIPTION: SEQ ID NO:7:

```
   Ser  Gln  Gly  Thr  Phe  Thr  Ser  Xaa  Tyr  Ser  Lys  Tyr  Leu  Asp  Ala
   1                   5                        10                       15

Arg  Arg  Ala  Gln  Asp  Phe  Val  Gln  Trp  Leu  Met  Asn  Thr
                       20                       25
```

(2) INFORMATION FOR SEQ ID NO:8:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide
        (A) DESCRIPTION: glucagon amide (iii) HYPOTHETICAL: No (iv) ANTI-SENSE: NO (ix) FEATURE:
        (A) NAME/KEY: amide group substitution for carboxyl group
        (D) OTHER INFORMATION: Xaa represents Nle (xi) SEQUENCE DESCRIPTION: SEQ ID NO:8:

```
   His  Ser  Gln  Gly  Thr  Phe  Thr  Ser  Xaa  Tyr  Ala  Lys  Tyr  Leu  Asp  Gln
   1                        5                        10                       15

Arg  Arg  Ala  Gln  Asp  Phe  Val  Gln  Trp  Leu  Met  Asn  Thr
                       20                       25
```

(2) INFORMATION FOR SEQ ID NO:9:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide
        (A) DESCRIPTION: glucagon amide (iii) HYPOTHETICAL: No (iv) ANTI-SENSE: NO (ix) FEATURE:
        (A) NAME/KEY: amide group substitution for carboxyl group
        (D) OTHER INFORMATION: Xaa represents Nle ( x i ) SEQUENCE DESCRIPTION: SEQ ID NO:9:

His Ser Gln Gly Thr Phe Thr Ser Xaa Tyr Ala Lys Tyr Leu Asp Ala
1               5                   10                  15

Arg Arg Ala Gln Asp Phe Val Gln Trp Leu Met Asn Thr
            20                  25

( 2 ) INFORMATION FOR SEQ ID NO:10:

( i ) SEQUENCE CHARACTERISTICS:
      ( A ) LENGTH: 28 amino acids
      ( B ) TYPE: amino acid
      ( C ) STRANDEDNESS: single
      ( D ) TOPOLOGY: linear ( i i ) MOLECULE TYPE: peptide
      ( A ) DESCRIPTION: glucagon amide ( i i i ) HYPOTHETICAL: No ( i v ) ANTI-SENSE: NO ( i x ) FEATURE:
      ( A ) NAME/KEY: amide group substitution for carboxyl group
      ( D ) OTHER INFORMATION: Xaa represents Nle ( x i ) SEQUENCE DESCRIPTION: SEQ ID NO:10:

Ser Gln Gly Thr Phe Thr Ser Xaa Tyr Ala Lys Tyr Leu Asp Ala
1               5                   10                  15

Arg Arg Ala Gln Asp Phe Val Gln Trp Leu Met Asn Thr
            20                  25

( 2 ) INFORMATION FOR SEQ ID NO:11:

( i ) SEQUENCE CHARACTERISTICS:
      ( A ) LENGTH: 28 amino acids
      ( B ) TYPE: amino acid
      ( C ) STRANDEDNESS: single
      ( D ) TOPOLOGY: linear ( i i ) MOLECULE TYPE: peptide
      ( A ) DESCRIPTION: glucagon amide ( i i i ) HYPOTHETICAL: No ( i v ) ANTI-SENSE: NO ( i x ) FEATURE:
      ( A ) NAME/KEY: amide group substitution for carboxyl group ( x i ) SEQUENCE DESCRIPTION: SEQ ID NO:11:

Ser Gln Gly Thr Phe Thr Ser Trp Tyr Ala Lys Tyr Leu Asp Ala
1               5                   10                  15

Arg Arg Ala Gln Asp Phe Val Gln Trp Leu Met Asn Thr
            20                  25

( 2 ) INFORMATION FOR SEQ ID NO:12:

( i ) SEQUENCE CHARACTERISTICS:
      ( A ) LENGTH: 28 amino acids
      ( B ) TYPE: amino acid
      ( C ) STRANDEDNESS: single
      ( D ) TOPOLOGY: linear ( i i ) MOLECULE TYPE: peptide
      ( A ) DESCRIPTION: glucagon amide ( i i i ) HYPOTHETICAL: No ( i v ) ANTI-SENSE: NO ( i x ) FEATURE:

( A ) NAME/KEY: amide group substitution for carboxyl group ( x i ) SEQUENCE DESCRIPTION: SEQ ID NO:12:

Ser Gln Gly Thr Phe Thr Ser Leu Tyr Ala Lys Tyr Leu Asp Ala
1               5                   10                  15

Arg Arg Ala Gln Asp Phe Val Gln Trp Leu Met Asn Thr
                20                  25

( 2 ) INFORMATION FOR SEQ ID NO:13:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide
        ( A ) DESCRIPTION: glucagon amide ( i i i ) HYPOTHETICAL: No ( i v ) ANTI-SENSE: NO ( i x ) FEATURE:
        ( A ) NAME/KEY: amide group substitution for carboxyl group ( x i ) SEQUENCE DESCRIPTION: SEQ ID NO:13:

Ser Gln Gly Thr Phe Thr Ser Phe Tyr Ala Lys Tyr Leu Asp Ala
1               5                   10                  15

Arg Arg Ala Gln Asp Phe Val Gln Trp Leu Met Asn Thr
                20                  25

( 2 ) INFORMATION FOR SEQ ID NO:14:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide
        ( A ) DESCRIPTION: glucagon amide ( i i i ) HYPOTHETICAL: No ( i v ) ANTI-SENSE: NO ( i x ) FEATURE:
        ( A ) NAME/KEY: amide group substitution for carboxyl group ( x i ) SEQUENCE DESCRIPTION: SEQ ID NO:14:

Ser Gln Gly Thr Phe Thr Ser Glu Tyr Ala Lys Tyr Leu Asp Ala
1               5                   10                  15

Arg Arg Ala Gln Asp Phe Val Gln Trp Leu Met Asn Thr
                20                  25

( 2 ) INFORMATION FOR SEQ ID NO:15:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide
        ( A ) DESCRIPTION: glucagon amide ( i i i ) HYPOTHETICAL: No ( i v ) ANTI-SENSE: NO ( i x ) FEATURE:
        ( A ) NAME/KEY: amide group substitution for carboxyl group ( x i ) SEQUENCE DESCRIPTION: SEQ ID NO:15:

Ser Gln Gly Thr Phe Thr Ser Glu Tyr Ala Lys Tyr Leu Asp Ala
1               5                   10                  15

Lys Lys Ala Gln Glu Phe Val Gln Trp Leu Met Asn Thr
                20                  25

( 2 ) INFORMATION FOR SEQ ID NO:16:

( i ) SEQUENCE CHARACTERISTICS:
            ( A ) LENGTH: 28 amino acids
            ( B ) TYPE: amino acid
            ( C ) STRANDEDNESS: single
            ( D ) TOPOLOGY: linear ( i i ) MOLECULE TYPE: peptide
            ( A ) DESCRIPTION: glucagon analog ( i i i ) HYPOTHETICAL: No ( i v ) ANTI-SENSE: NO ( i x ) FEATURE:
            ( D ) OTHER INFORMATION: Xaa represents Nle ( x i ) SEQUENCE DESCRIPTION: SEQ ID NO:16:

Ser Gln Gly Thr Phe Thr Ser Xaa Tyr Ser Lys Tyr Leu Asp Ala
1               5                   10                  15

Arg Arg Ala Gln Asp Phe Val Gln Trp Leu Met Asn Thr
                20                  25

( 2 ) INFORMATION FOR SEQ ID NO:17:

( i ) SEQUENCE CHARACTERISTICS:
            ( A ) LENGTH: 29 amino acids
            ( B ) TYPE: amino acid
            ( C ) STRANDEDNESS: single
            ( D ) TOPOLOGY: linear ( i i ) MOLECULE TYPE: peptide
            ( A ) DESCRIPTION: glucagon analog ( i i i ) HYPOTHETICAL: No ( i v ) ANTI-SENSE: NO ( i x ) FEATURE:
            ( D ) OTHER INFORMATION: Xaa represents Nle ( x i ) SEQUENCE DESCRIPTION: SEQ ID NO:17:

His Ser Gln Gly Thr Phe Thr Ser Xaa Tyr Ala Lys Tyr Leu Asp Gln
1               5                   10                  15

Arg Arg Ala Gln Asp Phe Val Gln Trp Leu Met Asn Thr
                20                  25

( 2 ) INFORMATION FOR SEQ ID NO:18:

( i ) SEQUENCE CHARACTERISTICS:
            ( A ) LENGTH: 29 amino acids
            ( B ) TYPE: amino acid
            ( C ) STRANDEDNESS: single
            ( D ) TOPOLOGY: linear ( i i ) MOLECULE TYPE: peptide
            ( A ) DESCRIPTION: glucagon analog ( i i i ) HYPOTHETICAL: No ( i v ) ANTI-SENSE: NO ( i x ) FEATURE:
    ( D ) OTHER INFORMATION: Xaa represents Nle ( x i ) SEQUENCE DESCRIPTION: SEQ ID NO:18:

```
His Ser Gln Gly Thr Phe Thr Ser Xaa Tyr Ala Lys Tyr Leu Asp Ala
 1               5                  10                  15
Arg Arg Ala Gln Asp Phe Val Gln Trp Leu Met Asn Thr
             20                  25
```

( 2 ) INFORMATION FOR SEQ ID NO:19:

( i ) SEQUENCE CHARACTERISTICS:
    ( A ) LENGTH: 28 amino acids
    ( B ) TYPE: amino acid
    ( C ) STRANDEDNESS: single
    ( D ) TOPOLOGY: linear ( i i ) MOLECULE TYPE: peptide
    ( A ) DESCRIPTION: glucagon analog ( i i i ) HYPOTHETICAL: No ( i v ) ANTI-SENSE: NO ( i x ) FEATURE:
    ( D ) OTHER INFORMATION: Xaa represents Nle ( x i ) SEQUENCE DESCRIPTION: SEQ ID NO:19:

```
Ser Gln Gly Thr Phe Thr Ser Xaa Tyr Ala Lys Tyr Leu Asp Ala
 1               5                  10                  15
Arg Arg Ala Gln Asp Phe Val Gln Trp Leu Met Asn Thr
             20                  25
```

( 2 ) INFORMATION FOR SEQ ID NO:20:

( i ) SEQUENCE CHARACTERISTICS:
    ( A ) LENGTH: 28 amino acids
    ( B ) TYPE: amino acid
    ( C ) STRANDEDNESS: single
    ( D ) TOPOLOGY: linear ( i i ) MOLECULE TYPE: peptide
    ( A ) DESCRIPTION: glucagon analog ( i i i ) HYPOTHETICAL: No ( i v ) ANTI-SENSE: NO ( x i ) SEQUENCE DESCRIPTION: SEQ ID NO:20:

```
Ser Gln Gly Thr Phe Thr Ser Trp Tyr Ala Lys Tyr Leu Asp Ala
 1               5                  10                  15
Arg Arg Ala Gln Asp Phe Val Gln Trp Leu Met Asn Thr
             20                  25
```

( 2 ) INFORMATION FOR SEQ ID NO:21:

( i ) SEQUENCE CHARACTERISTICS:
    ( A ) LENGTH: 28 amino acids
    ( B ) TYPE: amino acid
    ( C ) STRANDEDNESS: single
    ( D ) TOPOLOGY: linear ( i i ) MOLECULE TYPE: peptide
    ( A ) DESCRIPTION: glucagon analog ( i i i ) HYPOTHETICAL: No ( i v ) ANTI-SENSE: NO ( x i ) SEQUENCE DESCRIPTION: SEQ ID NO:21:

Ser Gln Gly Thr Phe Thr Ser Leu Tyr Ala Lys Tyr Leu Asp Ala
1               5                   10                  15

Arg Arg Ala Gln Asp Phe Val Gln Trp Leu Met Asn Thr
            20                  25

(2) INFORMATION FOR SEQ ID NO:22:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: peptide
        (A) DESCRIPTION: glucagon analog (iii) HYPOTHETICAL: No (iv) ANTI-SENSE: NO (xi) SEQUENCE DESCRIPTION: SEQ ID NO:22:

Ser Gln Gly Thr Phe Thr Ser Phe Tyr Ala Lys Tyr Leu Asp Ala
1               5                   10                  15

Arg Arg Ala Gln Asp Phe Val Gln Trp Leu Met Asn Thr
            20                  25

(2) INFORMATION FOR SEQ ID NO:23:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: peptide
        (A) DESCRIPTION: glucagon analog (iii) HYPOTHETICAL: No (iv) ANTI-SENSE: NO (xi) SEQUENCE DESCRIPTION: SEQ ID NO:23:

Ser Gln Gly Thr Phe Thr Ser Glu Tyr Ala Lys Tyr Leu Asp Ala
1               5                   10                  15

Arg Arg Ala Gln Asp Phe Val Gln Trp Leu Met Asn Thr
            20                  25

(2) INFORMATION FOR SEQ ID NO:24:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: peptide
        (A) DESCRIPTION: glucagon analog (iii) HYPOTHETICAL: No (iv) ANTI-SENSE: NO (xi) SEQUENCE DESCRIPTION: SEQ ID NO:24:

Ser Gln Gly Thr Phe Thr Ser Glu Tyr Ala Lys Tyr Leu Asp Ala
1               5                   10                  15

Lys Lys Ala Gln Glu Phe Val Gln Trp Leu Met Asn Thr
            20                  25

(2) INFORMATION FOR SEQ ID NO:25:

(i) SEQUENCE CHARACTERISTICS:
    (A) LENGTH: 29 amino acids
    (B) TYPE: amino acid
    (C) STRANDEDNESS: single
    (D) TOPOLOGY: linear (ii) MOLECULE TYPE: peptide
    (A) DESCRIPTION: glucagon amide (iii) HYPOTHETICAL: No (iv) ANTI-SENSE: NO (ix) FEATURE:
    (A) NAME/KEY: amide group substitution for carboxyl group (xi) SEQUENCE DESCRIPTION: SEQ ID NO:25:

His Ser Gln Gly Thr Phe Thr Ser Asp Tyr Ser Lys Tyr Leu Asp Ser
 1               5                  10                      15

Arg Arg Ala Gln Asp Phe Val Gln Trp Leu Met Asn Thr
         20                  25

GLUCAGON ANALOGS WITH SERINE REPLACEMENTS

This application is a continuation-in-part of U.S. Ser. No. 08/255,558, filed Jun. 8, 1994, now U.S. Pat. No. 5,480,867 which is a continuation of U.S. Ser. No. 08/175,137, filed Dec. 29, 1993, now abandoned.

This invention was made with Government support under U.S. Public Health Grant DK24039. The Government has certain rights in this invention.

BACKGROUND OF THE INVENTION

Glucagon is a 29-residue peptide hormone that regulates glycogenesis. The structure of glucagon may be represented as follows:

```
His-Ser-Gln-Gly-Thr-Phe-Thr-Ser-Asp-Tyr-Ser-Lys-Tyr-Leu-
 1   2   3   4   5   6   7   8   9   10  11  12  13  14

Asp-Ser-Arg-Arg-Ala-Gln-Asp-Phe-Val-Gln-Trp-Leu-Met-Asn-
 15  16  17  18  19  20  21  22  23  24  25  26  27  28

Thr    SEQ ID NO: 1
 29
```

The abbreviations utilized herein are those recommended by IUPAC-IUB [See Eur. J. Biochemo 138, 9 (1984)].

The nomenclature used to define the peptides is that specified by Schroder & Lubke, "The Peptides", Academic Press (1965), wherein in accordance with conventional representation the amino group at the N-terminal appears to the left and the carboxyl group at the C-terminal to the right. Where the amino acid residue has isomeric forms, it is the L- or naturally occurring form of the amino acid that is represented unless otherwise expressly indicated.

Insulin, as is known, rapidly decreases elevated blood sugar. It is believed that, in humans, diabetes is only observed when insulin levels are low and glucagon levels are simultaneously elevated. The absence of insulin causes a rapid increase in blood glucose. Large amounts of insulin are required to reduce the glucose levels to normal. The maintenance of stable levels is difficult and subject to considerable fluctuation. This wide fluctuation is responsible, at least in part, for the clinical difficulties experienced in diabetes.

Glucagon appears to act by binding to liver membrane receptors thereby activating adenylate cyclase which, in turn, triggers a series of reactions including the production of cyclic adenosine monophosphate (cAMP), which activates phosphorylase and inhibits glycogen synthetase, thereby contributing to elevated glucose levels in the blood.

Recently, considerable effort has been expended to develop glucagon antagonists that will bind to liver membrane receptors but do not have the ability to transduce the signal to activate adenylate cyclase. One such product is Nα-trinitrophenyl [12-homoarginine] glucagon. This product does bind to the glucagon receptor without significant activation of adenylate cyclase. It also activates another signaling system in the hepatocyte membrane leading to the production of inositol trisphosphate and calcium ions. A useful antagonist will block the action of endogenous glucagon by preventing it from binding to the liver membrane receptors and thereby producing cAMP and glucose in the cell, and the ultimate elevation of blood sugar. Such products would be useful to reduce a diabetic's need for injections or infusion of insulin.

An ideal glucagon antagonist would (1) be completely inactive toward stimulation of adenylate cyclase and production of cAMP, (2) bind as well as, or better than, glucagon itself to the liver membrane receptor, (3) compete with glucagon for receptor binding, (4) at moderate concentrations fully inhibit the action of glucagon toward the activation of adenylate cyclase, and (5) have a satisfactory inhibition index.

The inhibition index is the molar ratio of antagonist to agonist which reduces the biological response to 50% of the value in the absence of antagonist. It will be discussed more fully hereinafter.

U.S. Pat. Nos. 4,879,273 and 5,143,902 describe certain useful glucagon analogs in which the aspartic acid residue at the 9-position of the glucagon molecule is removed or replaced with another amino acid residue either in the D-form or the L-form. The replacement may be selected from any of a number of amino acids both natural and synthetic, including hydrophobic and hydrophilic amino acids, aliphatic amino acids, aryl amino acids, basic amino acids and acidic amino acids.

It was observed that compounds of the class described in these patents either with or without the histidine residue at the 1-position are useful adjuncts to insulin therapy in the control of blood glucose levels. The preferred compounds for such utility, as disclosed in the prior patents are:

des His$^1$[Gly$^9$]glucagon SEQ ID NO: 2 des His$^1$[Nle$^9$]glucagon SEQ ID NO: 3 des His$^1$[Lys$^9$]glucagon SEQ ID NO: 4 des His$^1$[Glu$^9$]glucagon SEQ ID NO: 5 des His$^1$[Glu$^9$Lys$^{17,18}$Glu$^{21}$]glucagon SEQ ID NO: 6 and the corresponding carboxy terminal amides of such compounds.

It has now been discovered that the utility of the compounds of the previous patents for the treatment of diabetes can be remarkably and surprisingly improved by replacement of the serine residue at the 16-position and the optional replacement of the serine residue at the 11-position and/or the aspartic acid residue at the 21-position. However, the key to the utility of the compounds is still the 9-position.

SUMMARY OF THE INVENTION

A novel class of glucagon antagonists has now been discovered which substantially fulfills the criteria listed above with surprising improvements and minimum side effects. These compounds are analogs of the peptide glucagon, His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr, SEQ ID NO: 1 characterized by the deletion or replacement of the aspartic acid residue at the 9-position and with replacement Of the serine residue at the 16-position, and the optional replacement of amino acid residues at other positions.

DETAILED DESCRIPTION OF THE INVENTION

The novel glucagon analogs of the present invention, in addition to the position modifications outlined above, are characterized by a binding activity of at least about 40% relative to glucagon, an inhibition index less than 10 and an adenylate cyclase activity less than 1% that of glucagon. These remarkably improved therapeutic parameters have been made possible by the discovery of the significant contribution to binding and transduction made possible by modifications in the glucagon molecule at positions other than the 1- and the 9-positions, especially by modifications of the 11- and 16-positions.

The replacement amino acid residues at the 16-position and, if desired, at the 11- and 21-positions, are selected from among natural and synthetic aliphatic amino acids, preferably those containing up to five carbon atoms, either in the D-form or the L-form. Preferred replacement amino acid residues at the 9-position are phenylalanine (Phe), leucine (Leu), norleucine (Nle), glutamic acid (Glu) and tryptophan (Trp), and at the 11-and 16-positions, alanine (Ala) and leucine (Leu).

It has been observed that, generally, deletion of the histidine residue at the 1-position improves the desirable characteristics of the products of this invention.

The glucagon analogs of this invention also include derivatives having the defined properties. As indicated above, C-terminal amides are actually preferred over the C-terminal carboxyl compounds. Side chain amides such as amides of dibasic acids are also useful. Esters, especially those based on alkyl or aralkyl alcohols corresponding to the amides, may also be employed. Ethers, especially lower alkyl ethers of analogs including Ser, Thr and Tyr amino acid residues are also useful, as are esters of these analogs based on alkyl, aryl and aralkyl acids. Glucagon analogs containing amino acid residues with additional functional groups may also be converted to derivatives within the scope of the invention. These can include, for example, N-acetyl derivatives of diamino acids, such as lysine.

One class of useful derivatives is based on des-His$^1$ glucagon analogs in which the amino group of the amino terminal serine residue has been converted to a 2,4-difluorobenzoyl amide. Other hydroxyl and amine substituted amino acids derivatized with 2,4-difluorobenzoic acid are within the scope of the invention whether or not the histidyl residue at the 1-position is in place.

In some instances, compounds within the scope of the invention may be synthesized and thereafter utilized with one or more of the blocking groups still in place.

The products of this invention can be and have been synthesized by known solid phase techniques. See, for example, Barany and Merrifield (1979) in The Peptides, eds. Gross and Meienhofer (Academic Press, New York) Vol. 2A, Pages 1–284. The products can be prepared by manual methods or, for example, on a peptide synthesizer such as the Applied Biosystems 430 unit.

The glucagon analogs of the present invention with a free C-terminal carboxyl were synthesized on phenylacetamidomethyl-resin supports, and those with C-terminal amides were made on a methylbenzhydrylamine-resin. Side chain protection was as follows: Arg(Tos), Asp (OcHx), Glu(OcHx), His(Tos), Lys(ClZ), Ser(Bzl), Thr (Bzl), Trp(For), and Tyr(BrZ). Double couplings with preformed symmetric anhydrides in dimethylformamide were used routinely for all tert-butyloxycarbonyl-protected amino acids except for tosyl arginine, glutamine, and asparagine, where N-hydroxybenzotriazole esters in dimethylformamide were required [Konig, W. & Gieger, R. Chem. Ber. 103, 788 (1970)].

The tert-Butyloxycarbonyl (Boc) protected amino acids utilized in the synthetic procedures described herein are commercially available, e.g., from Peninsula Laboratories, (San Carlos, Calif.) The p-methylbenzhydrylamine resin (0.45 mmol/g) is likewise available from United States Biochemical (Cleveland, Ohio) and boc-Thr-(Bzl)-4-oxymethylphenylacetamidomethyl copoly (styrene-1% divinyl benzene) is preparable as described by Mitchell et al., J. Org. Chem. 43, 2845 (1978), and is commercially available.

The assembled protected peptide-resins were cleaved by the "low/high HF" technique [Tam, J. P.; Heath, W. F. & Merrifield, R. B., J. Am. Chem. Soc. 105, 6442 (1983)], which was developed to avoid a number of potential side reactions. After evaporation of HF and washing with ether, the crude free peptide was extracted with 10% acetic acid and lyophilized. Purification of the synthetic peptides was performed by preparative low-pressure reverse-phase liquid chromatography on $C_{18}$-silica as described [Andreu, D. & Merrifield, R. B. in Peptides: Structure and Function, eds. Deber, C. M.; Hruby, V. J. & Kopple, K. D. (Pierce Chem. Co., Rockford, Ill.), pp. 595–598. The overall yields were between 35 and 40%. Homogeneity was demonstrated by analytical HPLC, and identity was confirmed by amino acid analysis, and molecular weight determined by mass spectroscopy.

The amino acid analysis, of all compounds prepared agreed with theory within ±5%, and the molecular weights determined by mass spectrometry were within 0.5 mass units.

The following compounds of the present invention were prepared in accordance with the above-described methods:

des-His$^1$Nle$^9$Ala$^{16}$ glucagon amide; SEQ ID NO: 7

Nle$^9$Ala$^{11}$Gln$^{16}$ glucagon amide; SEQ ID NO: 8

Nle$^9$Ala$^{11}$Ala$^{16}$ glucagon amide; SEQ ID NO: 9 des-His$^1$Nle$^9$Ala$^{11}$Ala$^{16}$ glucagon amide; SEQ ID NO: 10 des-His$^1$Trp$^9$Ala$^{11}$Ala$^{16}$ glucagon amide; SEQ ID NO: 11 des-His$^1$Leu$^9$Ala$^{11}$Ala$^{16}$ glucagon amide; SEQ ID NO: 12 des-His$^1$Phe$^9$Ala$^{11}$Ala$^{16}$ glucagon amide; SEQ ID NO: 13 des-His$^1$Nle$^9$Ala$^{11}$Gln$^{16}$ glucagon amide; SEQ ID NO: 14 des-His$^1$Glu$^9$Ala$^{11}$Ala$^{16}$Glu$^{21}$ glucagon amide SEQ ID NO: 15; and the corresponding carboxy terminal compounds thereof SEQ ID NO: 16–24.

Various tests were employed to determine the efficacy of the products of this invention. These included the membrane receptor binding assay and adenyl cyclase assays.

In these assays, the $^{125}$I-labeled glucagon, available from New England Nuclear, was used without further purification for periods up to 1 month after its preparation. Creatine phosphate, creatine kinase, bovine serum albumin, dithiothreitol, GTP, and ATP, are commercially available, e.g., from Sigma, and the cAMP assay kit containing [8-$^3$H] cAMP was obtained from Amersham. Durapore membrane filters (0.45 um) were from Millipore.

Membrane Binding Assay

Liver plasma membranes were prepared from male Sprague-Dawley rats (Charles River Breeding Laboratories) by the Neville procedure as described by Pohl [Pohl, S. L. (1976) in Methods in Receptor Research, ed. Blecher, M. (Marcel Dekker, New York), pp. 160–164]. The receptor binding assay was as described by Wright and Rodbell [Wright, D. E. & Rodbell, M. (1979) J. Bio. Chem. 254, 268–269] in which competition for glucagon receptors between $^{125}$I-labeled natural glucagon (1.6 nM) and the unlabeled synthetic analog was measured. After correction for the blank, the percentage of displacement of label was compared with that of a purified glucagon standard, and the relative binding affinity was calculated.

Adenylate Cyclase Assay

The assay on liver membranes was performed according to Salomon et al. [Salomon, Y; Londos, C. & Rodgell, M., Anal. Biochem. 58, 541, 548 (1974)]. The released cAMP was mixed with [8-$^3$H] cAMP measured with a high affinity cAMP binding protein.

The purpose of the membrane binding assay is to measure the ability of analogs of glucagon to bind to liver membrane receptor compared to that of glucagon.

When the glucagon analogs of this invention were assayed, they were assayed as amides with natural glucagon amide as a standard, thus eliminating the possibility of imprecision due to the heterogeneity of membrane preparations. In fact, it presently appears that C-terminal amides are more active than the corresponding carboxyl compounds. Accordingly, the C-terminal amides of the glucagon analogs of the invention are highly preferred compounds of the invention.

The relative binding affinity of a given analog is expressed as:

$$\frac{\text{(half maximal displacement concentration of glucagon)}}{\text{(half maximal displacement concentration of analog)}} \times 100$$

The purpose of the adenylate cyclase assay is to measure the ability of the compound under test to stimulate the activity of adenylate cyclase. The assays are used to measure relative potency, maximum activity and inhibition index.

The inhibition index, defined above, was determined from adenylate cyclase assays by two different protocols.

1. A glucagon standard curve for cAMP vs. glucagon concentration was established. Then another glucagon assay curve was measured in the presence of a constant amount of antagonist. The concentration of glucagon that had its activity reduced to 50% by that concentration of inhibitor was then determined.

2. A series of tubes were set up containing an amount of glucagon which will produce 90% of maximum response. Increasing amounts of antagonist were then added and the concentration that reduced the response to 45% of maximum was determined.

The compounds of this invention were found to have an inhibition index less than 10, membrane receptor binding activity of at least 40% compared to glucagon and an adenylate cyclase activity which is less than 1% of glucagon.

In the most preferred compounds of this invention, the $pA_2$ value is at least 5 and preferably above 7.

The $pA_2$ value is the negative logarithm of the concentration of antagonist that reduces the response to 1 unit of agonist to the response obtained from 0.5 unit of agonist.

The following table shows the results of measurements with glucagon and certain of the presently preferred compounds of this invention measured as amides.

The products of this invention will generally be administered in the same manner as insulin, i.e., parenterally, or by infusion. Since their chemical structure and activity is quite similar to insulin, they will generally be administered with the same types of pharmaceutically acceptable excipients as insulin. They may in fact be coadministered with insulin in the same dosage units. They may also be administered simultaneously with the insulin although not in the same composition.

Since the products of the invention are amphoteric, they may be utilized as free bases, as acid addition salts, or as metal salts. The salts must, of course, be pharmaceutically acceptable, and these will include metal salts, particularly alkali and alkaline earth metal salts, and typically potassium or sodium salts. A wide variety of pharmaceutically acceptable acid addition salts are available. These include those prepared from both organic and inorganic acids, preferably mineral acids. Typical acids, which may be mentioned by way of example, include citric, succinic, lactic, hydrochloric and hydrobromic acids. Such products are readily prepared by procedures well known to those skilled in the art.

The products of the invention will normally be provided for as parenteral compositions for injection or infusion. They can, for example, be suspended in an inert oil, suitably a vegetable oil such as sesame, peanut, or olive oil. Alternatively, they can be suspended in an aqueous isotonic buffer solution at a pH of about 5.6 to 74. Useful buffers include sodium citrate-citric acid and sodium phosphate-phosphoric acid.

The desired isotonicity may be accomplished using sodium chloride or other pharmaceutically acceptable agents, such as dextrose, boric acid, sodium tartrate, propylene glycol, or other inorganic or organic solutes. Sodium chloride is preferred, particularly when the buffer contains sodium ions.

If desired, the solutions may be thickened with a thickening agent such as methyl cellulose. They may be prepared in emulsified form, either water in oil or oil in water. Any of a wide variety of pharmaceutically acceptable emulsifying agents may be employed including, for example, acacia powder, or an alkaryl polyether alcohol sulfate or sulfonate such as Triton.

The therapeutically useful compositions of the invention are prepared by mixing the ingredients following generally accepted procedures. For example, the selected components may be simply mixed in a blender or other standard device to produce a concentrated mixture which may then be adjusted to the final concentration and viscosity by the addition of water or thickening agent and, optionally, a buffer to control pH or an additional solute to control tonicity.

TABLE 1

| Analog of Glucagon Amide | % Binding Activity | % Relative Activity | $(I/A)_{50}$ | $pA_2$ |
|---|---|---|---|---|
| Glucagon Amide SEQ ID NO:25 | 100 | 15 | | |
| 1. Nle$^9$Ala$^{11}$Gln$^{16}$ SEQ ID NO:8 | 46.8 | 0.003 | 1.6 | 8.7 |
| 2. des-His$^1$Nle$^9$Ala$^{16}$ SEQ ID NO:7 | 100 | 0.001 | 2.14 | 8.4 |
| 3. des-His$^1$Nle$^9$Ala$^{11}$Ala$^{16}$ SEQ ID NO:10 | 100 | <0.0043 | 0.85 | 8.4 |
| 4. des-His$^1$Nle$^9$Ala$^{11}$Gln$^{16}$ SEQ ID NO:14 | 56.3 | 0.0011 | 2.2 | 8.4 |
| 5. des-His$^1$Glu$^9$Ala$^{11}$Ala$^{16}$Glu$^{21}$ SEQ ID NO:15 | 39 | 0.016 | 2.57 | 8.5 |
| 6. des-His$^1$Phe$^9$Ala$^{11}$Ala$^{16}$ SEQ ID NO:13 | 129 | <0.001 | 2.31 | 8.35 |
| 7. des-His$^1$Leu$^9$Ala$^{11}$Ala$^{16}$ SEQ ID NO:12 | 182 | <0.001 | 0.93 | 8.9 |
| 8. des-His$^1$Trp$^9$Ala$^{11}$Ala$^{16}$ SEQ ID NO:11 | 36 | 0.17 | 3.7 | 7.7 |
| 9. Nle$^9$Ala$^{11}$Ala$^{16}$ SEQ ID NO:9 | 47 | <0.003 | 1.6 | 8.7 |

For use by the physician, the compositions will be provided in unit dosage form containing an amount of glucagon analog which will be effective in one or multiple doses to control glucogenesis and ketogenesis at the selected level, normally in the presence of insulin. As will be recognized by those skilled in the art, an effective amount of the therapeutic agent will vary with many factors, including the age and weight of the patient, the amount of insulin which is concurrently employed, the blood sugar level to be obtained, the inhibition index of the selected analog, and other factors. Typical dosage units will contain from 0.2 to 0.8 eg/ml, although wide variations from this range are possible while yet achieving useful results.

What is claimed is:

1. A glucagon analog peptide wherein
   (a) histidine at the 1-position is either present or absent;
   (b) the aspartic acid residue at the 9-position is either absent or replaced with another amino acid residue;
   (c) the serine residue at the 11-position is optionally replaced with an aliphatic amino acid residue;
   (d) the serine residue at the 16-position is replaced with an aliphatic amino acid residue;
   (e) the aspartic acid residue at the 21-position is optionally replaced with an aliphatic amino acid residue; and
   (f) the carboxy terminus is optionally amidated;

said analog being further characterized by a relative membrane receptor binding activity compared to glucagon of at least about 40%, an inhibition index less than 10 and an adenylate cyclase activity less than 1% of that of glucagon; and pharmaceutically acceptable acid addition salts thereof wherein said analog is selected from the group consisting of wherein said analog is selected from the group consisting of des-His$^1$Nle$^9$Ala$^{16}$ glucagon (SEQ ID NO: 16), Nle$^9$Ala$^{11}$Gln$^{16}$ glucagon (SEQ ID NO: 17), Nle$^9$Ala$^{11}$Ala$^{16}$ glucagon (SEQ ID NO: 18) or the amide thereof (SEQ ID NO: 9), des-His$^1$Nle$^9$Ala$^{11}$Ala$^{16}$ glucagon (SEQ ID NO: 19), des-His$^1$Trp$^9$Ala$^{11}$Ala$^{16}$ glucagon (SEQ ID NO: 20) or the amide thereof (SEQ ID NO: 11), des-His$^1$Leu$^9$Ala$^{11}$Ala$^{16}$ glucagon (SEQ ID NO: 21) or the amide thereof (SEQ ID NO: 12), des-His$^1$Phe$^9$Ala$^{11}$Ala$^{16}$ glucagon (SEQ ID NO: 22), des-His$^1$Nle$^9$Ala$^{11}$Gln$^{16}$ glucagon (SEQ ID NO: 23), and des-His$^1$Glu$^9$Ala$^{11}$Ala$^{16}$Glu$^{21}$ glucagon (SEQ ID NO: 24).

2. The glucagon analog of claim 1 which is des-His$^1$Nle$^9$Ala$^{16}$ glucagon (SEQ ID NO: 16).

3. The glucagon analog of claim 1 which is Nle$^9$Ala$^{11}$Gln$^{16}$ glucagon (SEQ ID NO: 17).

4. The glucagon analog of claim 1 which is Nle$^9$Ala$^{11}$Ala$^{16}$ glucagon or the amide thereof (SEQ ID NO: 9).

5. The glucagon analog of claim 1 which is des-His$^1$Nle$^9$Ala$^{11}$Ala$^{16}$ glucagon (SEQ ID NO: 19).

6. The glucagon analog of claim 1 which is des-His$^1$Trp$^9$Ala$^{11}$Ala$^{16}$ glucagon (SEQ ID NO: 20) or the amide thereof (SEQ ID NO: 11).

7. The glucagon analog of claim 1 which is des-His$^1$Leu$^9$Ala$^{11}$Ala$^{16}$ glucagon (SEQ ID NO: 21) or the amide thereof (SEQ ID NO: 12).

8. The glucagon analog of claim 1 which is des-His$^1$Phe$^9$Ala$^{11}$Ala$^{16}$ glucagon (SEQ ID NO: 22) or the amide thereof (SEQ ID NO: 13).

9. The glucagon analog of claim 1 which is des-His$^1$Nle$^9$Ala$^{11}$Gln$^{16}$ glucagon (SEQ ID NO: 23).

10. The glucagon analog of claim 1 which is des-His$^1$Glu$^9$Ala$^{11}$Ala$^{16}$Glu$^{21}$ glucagon (SEQ ID NO: 24).

11. A pharmaceutical composition for control of glucogenesis in humans comprising an amount which is effective to achieve such control of a peptide consisting of a glucagon analog peptide wherein
   (a) histidine at the 1-position is either present or absent;
   (b) the aspartic acid residue at the 9-position is either absent or replaced with another amino acid residue;
   (c) the serine residue at the 11-position is optionally replaced with an aliphatic amino acid residue;
   (d) the serine residue at the 16-position is replaced with an aliphatic amino acid residue;
   (e) the aspartic acid residue at the 2-position is optionally replaced with an aliphatic amino acid residue; and
   (f) the carboxy terminus is optionally amidated;

said analog being further characterized by a relative membrane receptor binding activity of at least about 40% compared to glucagon, an inhibition index less than 10 and an adenylate cyclase activity which is less than 1% of that of glucagon; and the pharmaceutically acceptable acid addition salts thereof wherein said analog is selected from the group consisting of des-His$^1$Nle$^9$Ala$^{16}$ glucagon (SEQ ID NO: 16), Nle$^9$Ala$^{11}$Gln$^{16}$ glucagon (SEQ ID NO: 17), Nle$^9$Ala$^{11}$Ala$^{16}$ glucagon (SEQ ID NO: 18) or the amide thereof (SEQ ID NO: 9), des-His$^1$Nle$^9$Ala$^{11}$Ala$^{16}$ glucagon (SEQ ID NO: 19), des-His$^1$Trp$^9$Ala$^{11}$Ala$^{16}$ glucagon (SEQ ID NO: 20) or the amide thereof (SEQ ID NO: 11), des-His$^1$Leu$^9$Ala$^{11}$Ala$^{16}$ glucagon (SEQ ID NO: 21) or the amide thereof (SEQ ID NO: 12), des-His$^1$Phe$^9$Ala$^{11}$Ala$^{16}$ glucagon (SEQ ID NO: 22) des-His$^1$Nle$^9$Ala$^{11}$Gln$^{16}$ glucagon (SEQ ID NO: 23), and des-His$^1$Glu$^9$Ala$^{11}$Ala$^{16}$Glu$^{21}$ glucagon (SEQ ID NO: 24), together with a pharmaceutically acceptable carrier therefor.

12. The composition of claim 11 wherein the glucagon analog is des-His$^1$Nle$^9$Ala$^{16}$ glucagon (SEQ ID NO: 16).

13. The composition of claim 11 wherein the glucagon analog is Nle$^9$Ala$^{11}$Gln$^{16}$ glucagon (SEQ ID NO: 17).

14. The composition of claim 11 wherein the glucagon analog is Nle$^9$Ala$^{11}$Ala$^{16}$ glucagon (SEQ ID NO: 18) or the amide thereof (SEQ ID NO: 9).

15. The composition of claim 11 wherein the glucagon analog is des-His$^1$Nle$^9$Ala$^{11}$Ala$^{16}$ glucagon (SEQ ID NO: 19).

16. The composition of claim 11 wherein the glucagon analog is des-His$^1$Trp$^9$Ala$^{11}$Ala$^{16}$ glucagon (SEQ ID NO: 20) or the amide thereof (SEQ ID NO: 11).

17. The composition of claim 11 wherein the glucagon analog is des-His$^1$Leu$^9$Ala$^{11}$Ala$^{16}$ glucagon (SEQ ID NO: 21) or the amide thereof (SEQ ID NO: 12).

18. The composition of claim 11 wherein the glucagon analog is des-His$^1$Phe$^9$Ala$^{11}$Ala$^{16}$ glucagon (SEQ ID NO: 22) or the amide thereof (SEQ ID NO: 13).

19. The composition of claim 11 wherein glucagon analog is des-His$^1$Nle$^9$Ala$^{11}$Gln$^{16}$ glucagon (SEQ ID NO: 23).

20. The composition of claim 11 wherein the glucagon analog is des-His$^1$Glu$^9$Ala$^{11}$Ala$^{16}$Glu$^{21}$ glucagon (SEQ ID NO: 24).

21. The composition of claim 11 containing from about 0.2 to 0.8 µg/ml of a glucagon analog and a pharmaceutically acceptable carrier, formulated in unit dosage form for parenteral administration.

22. The composition of claim 21 wherein the glucagon analog is des-His$^1$Nle$^9$Ala$^{16}$ glucagon (SEQ ID NO: 16).

23. The composition of claim 21 wherein the glucagon analog is Nle$^9$Ala$^{11}$Gln$^{16}$ glucagon (SEQ ID NO: 17).

24. The composition of claim 21 wherein the glucagon analog is Nle$^9$Ala$^{11}$Ala$^{16}$ glucagon (SEQ ID NO: 18) or the amide thereof (SEQ ID NO: 9).

25. The composition of claim 21 wherein the glucagon analog is des-His$^1$Nle$^9$Ala$^{11}$Ala$^{16}$ glucagon (SEQ ID NO: 19).

26. The composition of claim 21 wherein the glucagon analog is des-His$^1$Trp$^9$Ala$^{11}$Ala$^{16}$ glucagon (SEQ ID NO: 20) or the amide thereof (SEQ ID NO: 11).

27. The composition of claim 21 wherein the glucagon analog is des-His$^1$Leu$^9$Ala$^{11}$Ala$^{16}$ glucagon (SEQ ID NO: 21) or the amide thereof (SEQ ID NO: 12).

28. The composition of claim 21 wherein the glucagon analog is des-His$^1$Phe$^9$Ala$^{11}$Ala$^{16}$ glucagon (SEQ ID NO: 22) or the amide thereof (SEQ ID NO: 13).

29. The composition of claim 21 wherein the glucagon analog is des -His$^1$Nle$^9$Ala$^{11}$Gln$^{16}$ glucagon (SEQ ID NO: 23).

30. The composition of claim 21 wherein the glucagon analog is des-His$^1$Glu$^9$Ala$^{11}$Ala$^{16}$Glu$^{21}$ glucagon (SEQ ID NO: 24).

* * * * *